United States Patent
Hruby et al.

(10) Patent No.: US 11,124,542 B2
(45) Date of Patent: *Sep. 21, 2021

(54) MODULATORS OF MELANOCORTIN RECEPTORS

(71) Applicant: ARIZONA BOARD OF REGENTS ON BEHALF OF THE UNIVERSITY OF ARIZONA, Tucson, AZ (US)

(72) Inventors: Victor J. Hruby, Tucson, AZ (US); Minying Cai, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,361

(22) Filed: Jun. 4, 2019

(65) Prior Publication Data

US 2019/0309022 A1 Oct. 10, 2019

Related U.S. Application Data

(63) Continuation of application No. 14/943,606, filed on Nov. 17, 2015, now abandoned, which is a continuation-in-part of application No. PCT/US2015/035180, filed on Jun. 10, 2015, which is a continuation-in-part of application No. 14/300,991, filed on Jun. 10, 2014.

(60) Provisional application No. 62/242,874, filed on Oct. 16, 2015, provisional application No. 62/017,137, filed on Jun. 25, 2014.

(51) Int. Cl.

| | |
|---|---|
| *C07K 7/64* | (2006.01) |
| *A61K 38/10* | (2006.01) |
| *A61K 9/00* | (2006.01) |
| *A61K 47/24* | (2006.01) |
| *A61K 9/107* | (2006.01) |
| *A61K 9/70* | (2006.01) |
| *C07K 14/68* | (2006.01) |
| *C07K 14/685* | (2006.01) |
| *C07K 14/72* | (2006.01) |
| *C07K 7/08* | (2006.01) |

(52) U.S. Cl.
CPC ............ *C07K 7/64* (2013.01); *A61K 9/0014* (2013.01); *A61K 9/107* (2013.01); *A61K 9/7084* (2013.01); *A61K 38/10* (2013.01); *A61K 47/24* (2013.01); *C07K 7/08* (2013.01); *C07K 14/68* (2013.01); *C07K 14/685* (2013.01); *C07K 14/723* (2013.01)

(58) Field of Classification Search
None
See application file for complete search history.

(56) References Cited

U.S. PATENT DOCUMENTS

| | | |
|---|---|---|
| 5,714,576 A | 2/1998 | Hruby et al. |
| 5,731,408 A | 3/1998 | Hadley et al. |
| 5,830,994 A | 11/1998 | D'Hinterland et al. |
| 6,228,840 B1 | 5/2001 | Wei et al. |
| 6,350,430 B1 | 2/2002 | Dooley et al. |
| 7,045,503 B1 | 5/2006 | McBride et al. |
| 7,160,873 B2 | 1/2007 | Magda et al. |
| 7,582,610 B2 | 9/2009 | Haskell-Luevano |
| 2005/0037951 A1 | 2/2005 | Blood et al. |
| 2005/0038230 A1 | 2/2005 | Sharma et al. |
| 2005/0187164 A1 | 8/2005 | Pinel |
| 2007/0270411 A1 | 11/2007 | Szewczyk et al. |
| 2009/0232838 A1 | 9/2009 | Dong et al. |
| 2010/0129319 A1 | 5/2010 | Lindquist et al. |
| 2015/0037376 A1 | 2/2015 | Seth et al. |

FOREIGN PATENT DOCUMENTS

| | | |
|---|---|---|
| WO | WO2005/079574 A1 | 9/2005 |
| WO | WO 2005-120588 | 12/2005 |
| WO | WO2006/037118 A1 | 4/2006 |
| WO | WO2008/071438 A2 | 6/2008 |
| WO | WO 2011-063367 | 5/2011 |

OTHER PUBLICATIONS

Grieco et al. ("Structure-Activity Studies of the Melanocortin Peptides: Discovery of Potent and Selective Affinity Antagonists for the hMC3 and hMC4 Receptors" J. Med. Chem 2002, 45, 5287-5294).*
Barkey NM et al., "Development of melanoma-targeted polymer micelles by conjugation of a Melanocortin 1 Receptor (MC 1 R) specific ligand" Journal of Medicinal Chemistry, 2011, 54(23):8078-8084.
Cai M et al., "Novel 3D Pharmacophore of a-MSH/y-MSH Hybrids Leads to Selective Human MCIR and MC3R Analogues" Journal of Medicinal Chemistry, 2005, 48(6):1839-1848.
Cai M et al., "Cell Signaling and Trafficking of Human Melanocortin Receptors in Real Time Using Two-photon Fluorescence and Confocal Laser Microscopy: Differentiation of Agonists and Antagonists" Chemical Biology & Drug Design, 2006, 68(4):183-93.
Cannan RK and Kibrick A, "Complex Formation between Carboxylic Acids and Divalent Metal Cations" Journal o/ the American Chemical Society, 1938, 60:2314-2320.
Chen J et al., "Melanoma-targeting Properties ofY9mTechnetium-labeled Cyclic u-Melanocyte-stimulating Hormone Peptide Analogues" Cancer Research, 2000, 60(20):5649-5658.

(Continued)

*Primary Examiner* — James H Alstrum-Acevedo
*Assistant Examiner* — Tara L Martinez
(74) *Attorney, Agent, or Firm* — Nguyen Tarbet LLC

(57) ABSTRACT

Modulators of melanocortin receptors (MCR) are provided herein. An MC5R peptide ligand is represented by to Formula 1:

$R_1$-Nle$^4$-c[Xaa$^5$-Yaa$^6$-(NMe)D-Nal(2')$^7$-Arg$^8$-Trp$^9$-(NMe)Zaa$^{10}$]-$R_2$.

$R_1$ can be an acetyl, a glycosylated amino acid, —CO—$(CH_2)_n CH_3$, or —CO—$(CH_2)_n CF_3$ with n ranging from 1 to 6. $R_2$ can be an —$CONH_2$, —COOH, or —$CH_2OH$. Xaa, Yaa, and Zaa can each be a natural amino acid or an unnatural amino acid.

4 Claims, 2 Drawing Sheets

Specification includes a Sequence Listing.

(56) References Cited

OTHER PUBLICATIONS

Chen J et al., "In vivo Evaluation of9YmTc/1?8Re-Labeled Linear Alpha-Melanocyte Stimulating Hormone Analogs for Specific Melanoma Targeting" Nuclear Medicine and Biology, 1999, 26(6):687-93.

Chrastina A et al., "Overcoming in vivo barriers to targeted nanodelivery" Interdisciplinary Reviews: Nanomedicine and Nanobiotechnology, 2011, 3(4):421-437.

Ehrlich J and Bogert MT, "Experiments in the Veratrole and Quinoxaline Groups" Journal o/Organic Chemistry, 1947, 12:522-534.

Hall JE et al., "Obesity-induced Hypertension: Role of Sympathetic Nervous System, Leptin, and Melanocortins" Journal 0/ Biological Chemistry, 2010, 285(23): 17271-17276.

Handl HL et al., "Lanthanide-based time-resolved fluorescence of in cyto ligand-receptor interactions" Analytical Biochemistry, 2004, 330(2):242-250.

Hu J et al., "Drug-Loaded and Superparamagnetic Iron Oxide Nanoparticle Surface-Embedded Amphiphilic Block Copolymer Micelles for Integrated Chemotherapeutic Drug Delivery and MR Imaging" Langmuir, 2012, 28 (4):2073-2082. Epub ahead of print(DOI: 1 0.1 021 II a203992q).

Jia Z et al., "One-Pot Conversion of RAFT-Generated Multifunctional Block Copolymers of HPMA to Doxorubicin Conjugated Acid- and Reductant-Sensitive Crosslinked Micelles" Biomacromolecules, 2008, 9(11 ):31 06-3113.

Jun D-J et al., "Melanocortins induce interleukin 6 gene expression and secretion through melanocortin receptors 2 and 5 in 3T3-LI adipocytes" Journal of Molecular Endocrinology, 2010,44:225-236.

Kedar U et al., "Advances in polymeric micelles for drug delivery and tumor targeting" Nanomedicine: Nanotechnology, Biology and Medicine, 2010, 6:714-729.

Kell Y JM et al., "Immobilized a-melanocyte stimulating hormone 10-13 (GKPV) inhibits tumor necrosis factor-a stimulated NF-KB activity" Peptides, 2006, 27(2):431-437.

Kessinger C et al., "In vivo angiogenesis imaging of solid tumors by avp3-targeted, dual-modality micellar nanoprobes" Experimental Biology and Medicine, 2010, 235:957-965.

Kim S et al., "Overcoming the barriers in micellar drug delivery: loading efficiency, in vivo stability, and micelle-cell interaction" Expert Opinion on Drug Delivery, 2010, 7(1):49-62.

Kim TH et al., "Evaluation of Temperature-Sensitive, Indocyanine Green-Encapsulating Micelles for Noninvasive Near-Infrared Tumor Imaging" Pharmaceutical Research, 2010, 27:1900-1913.

Koikov LN et al., "Sub-Nanomolar hMC1R Agonists by End-Capping of the Melanocortin Tetrapeptide His-D-Phe-Arg-Trp-NH2" Bioorganic & Medicinal Chemistry Letters, 2003, 13(16):2647-2650.

Koikov LN et al., Analogs of sub-nanomolar hMC1R agonist LK-184[Ph(CH2hCO-His-o-Phe-Arg-Trp-NH2J. An additional binding site within the human melanocortin receptor 1 T Bioorganic & Medicinal Chemistry Letters. 2004. 14:3997-4000.

Lee H et al., "The Effects of Particle Size and Molecular Targeting on the Intratumoral and Suncellular Distribution of Polymeric Nanoparticles" Molecular Pharmaceutics, 2010, 7(4):1195-1208.

Lee H et al., "In Vivo Distribution of Polymeric Nanoparticles at the Whole Body, Tumor and Cellular Levels" Pharmaceutical Research, 2010, 27(11):2343-2355.

Li J et al., "Redox-sensitive micelles self-assembled from amphiphilic hyaluronic acid-deoxycholic acid conjugates for targeted intracellular delivery of pac lit axel" Biomaterials, 2012, 33:2310-2320.

Li Y et al., "Well-Defined, Reversible Boronate Crosslinked Nanocarriers for Targeted Drug Delivery in Response to Acidic pH values and cis-Diols" Angewandte Chemie (International ed. in English), 2012 51:1-7.

Liu T et al., "Multifunctional pH-Disintegrable micellar nanoparticles of asymmetrically functionalized p-cyclodextrin-Based star copolymer covalently conjugated with doxorubicin and DOTA-Gd moieties" Biomaterials, 2012, 33:2521-2531.

Mayorov AV et al., "Effects of Macrocycle Size and Rigidity on Melanocortin Receptor-1 and -5 Selectivity in Cyclic Lactam a-Melanocyte-Stimulating Hormone Analogs" Chemical Biology & Drug Design, 2006, 67(5):329-335.

Oerlemans C et al., "Polymeric Micelles in Anticancer Therapy: Targeting, Imaging, and Triggered Release" Pharmaceutical Research, 2010, 27:2569-2589.

Poon Z et al., "Highly stable, ligand-clustered "patchy" micelle nanocarriers for systemic tumor targeting" Nanomedicine: Nanotechnology, Biology and Medicine, 2010, 7(2):201-209.

Rios-Doria J et al., "A Versatile Polymer Micelle Drug Delivery System for Encapsulation and In Vivo Stabilization of Hydrophobic Anticancer Drugs" Journal of Drug Delivery, 2012, 2012:951741, in press: Oct. 15, 2011.

Rodrigues AR et al., "Melanocortin 5 receptor activates ERKII2 through a PI3Kregulated signaling mechanism" Molecular and Cellular Endocrinology, 2009, 303:74-81.

Sawyer T et al., "4-Norleucine, 7-D-phenylalanine-a-melanocyte-stimulating hormone: A highly potent a-melanotropin with ultralong biological activity" Proceedings of the National Academy of Sciences, 1980, 77 (10):5754-5758.

Sessler JL et al., "Texaphyrins: Synthesis and Applications" Accounts of Chemical Research, 1994, 27:43-50.

Sessler JL et al., "New texaphyrin-type expanded porphyrins" Pure and Applied Chemistry, 1996, 68 (6):1291-1295.

Sessler JL and Miller RA? "Texaphyrins. New Drugs with Diverse Clinical Applications in Radiation and Photodynamic Therapy" Biochemical Pharmacology, 2000, 59:733-739.

Sessler JL et al., "Gadolinium(III) Texaphyrin: A Novel MRI Contrast Agent" Journal olthe American Chemical Society, 1993, 115(22):10368-10369.

Sessler JL et al., "Synthesis and Structural Characterization of Lanthanide(III) Texaphyrins" Inorganic Chemistry, 1993, 32:3175-3187.

Sessler JL et al., "An Expanded Porphyrin: The Synthesis and Structure of a New Aromatic Pentadentate Ligand" Journal o/the American Chemical Society, 1988, 110(16):5586-5588.

Shiraishi K et al., "Polyion complex micelle MRI contrast agents from Poly( ethylene glycol)-b-poly(L-lysine) block copolymers having Gd-DOT A; preparations and their control of T]-relaxivities and blood circulation characteristics" Journal o/Controlled Release, 2010, 148:160-167.

Siegrist W et al., "Characterization of Receptors for a-Melanocyte-stimulating Hormone on Human Melanoma Cells" Cancer Research, 1989, 49(22):6352-6358.

Sun T-M et al., "Simultaneous Delivery of siRNA and Pacilitaxel via a "Two-in-One" Micelleplex Promotes Synergistic Tumor Supression" ACS Nano, 2011, 5(2): 1483-1494.

Tang N et al., "Improving Penetration in Tumors with Nanoassemblies of Phospholipids and Doxorubicin" Journal of the National Cancer Institute, 2007, 99(13): 1 004-1 015.

Todorovic A et al., "N-Terminal Fatty Acylated His-DPhe-Arg-Trp-NH2 Tetrapeptides: Influence of Fatty Acid Chain Length on Potency and Selectivity at the Mouse Melanocortin Receptors and Human Melanocytes" Journal of Medicinal Chemistry, 2005, 48:3328-3336.

Van Der Ploeg LHT et al., "A role for the melanocortin 4 receptor in sexual function" Proceedings of the National Academy of Sciences, 2002, 99( 17): 11381-11386.

Viala 1 et al., "Phases IB and II Multidose Trial of Gadolinium Texaphyrin, a Radiation Sensitizer Detectable at MR Imaging: Preliminary Results in Brain Metastases" Radiology, 1999, 212(3):755-759.

Webb TR and Clark AIL, "Minireview: The Melanocortin 2 Receptor Accessory Proteins" Molecular Endocrinology, 2010, 24(3):475-484.

Xiong X-B and LA V Asanifar A, "Traceable Multifunctional Micellar Nanocarriers for Cancer-Targeted Co-delivery of MDR-I siRNA and Doxorubicin" ACS Nano, 2011, 5(6):5202-5213.

Yang R et al., "Galactose-Decorated Cross-Linked Biodegradable Poly(ethyleneglycol)-b-poly(£-caprolactone) Block Copolymer Micelles

(56) References Cited

OTHER PUBLICATIONS for Enhanced Hepatoma-Targeting Delivery of Pac litaxe I" Biomacromolecules, 2011, 12:3047-3055.
Yang X et al., "Tumor-Targeting. pH-Responsive, and Stable Unimolecular Micelles as Drug Nanocarriers for Targeted Cancer Therapy" Bioconjugate Chemistry, 2010, 21 (3):496-504.
Yang Y et al., "Novel Binding Motif of ACTH Analogues at the Melanocortin Receptors" Biochemistry, 2009, 48:9775-9784.
Yokoyama M, "Clinical Applications of Polymeric Micelle Carrier Systems in Chemotherapy and Image Diagnosis of Solid Tumors" Journal of Experimental and Clinical Medicine, 2011, 3(4):151-158.
Young SW et al., "Gadolinium(III) texaphyrin: A tumor selective radiation sensitizer that is detectable by MRI" Proceedings of the National Academy of Sciences, 1996, 93:6610-6615.
Plitas G and Ariyan CE, "Controversies in the Management of Regional Nodes in Melanoma" Journal of the National Comprehensive Cancer Network, 2012, 10:414-421.
Koo H et al., "In Vivo Targeted Delivery of Nanoparticles for Theranosis" Accounts of Chemical Research, 2011, 44 (10): 1 0 18-1 028.
Skinsight (http://www.skinsight.com/diseaseList.htm, accessed Apr. 14, 2015).
Merck Manual (http://www.merckmanuals.com/professional/dermatologic-disorders/cancers-of-the-skin/melanoma, accessed Apr. 14, 2015).
Abdel-Malek (Melanoma prevention strategy based on using tetrapeptide a-MSH analogs that protect human melanocytes from UV-induced DNA damage and cytotoxicity; The FASEB Journal; 20, E888-E896 (2006).
Choi et al. (Elastic vesicles as topical/transdermal drug delivery systems; International Journal of Cosmetic Science, 2005, 27, 211-221).
Shabsigh et al., Current Urology Reports, 2:463-467, Nov. 2001.
Kask et al. Endocrinology, 139: 5006-5014, 1998.
Lee et al. "Solution Structures and Molecular Interactions of Selective Melanocortin Receptor Antagonists," Mol. Cells, Dec. 31, 2010 (Dec. 31, 2010). vol. 30, pp. 551-556.
Lucas Doeoens et al: Journal of the American Chemical Society, vol. 132, No. 23, Jun. 16, 2010, pp. 8115-8128, XP055389484.
Victor J. Hruby et al: Annual Review of Pharmacology and Toxicology., vol. 53, No. 1, Jan. 6, 2013, pp. 557-580, XP055389581.
Yaniv Linde: "Structure-activity relationship and metabolic stability studies of backbone cyclization and N-methylation of melanocortin peptides—Linde—2008—Peptide Science—Wiley Online Library", Jul. 24, 2008, XP055389491, Retrieved from the Internet: URL:http://onlinelibrary.wiley.com/doi/10.1002/bip. 21057/full [retrieved on Jul. 10, 2017].
Zingsheim, Structure-Activity Study of a-N-Methylated SHU9119 Analogues, hMC4IR/TNF-a Antagonists, and Mutational Studies of the Melanocyte Stimulating Hormone Receptor, from the University of Arizona, OS/2009, pp. 1-66.
The NIH (https://rarediseases.info.nih .gov/diseases/diseases-by-category/17 /nervous-system-diseases) accessed Dec. 9, 2018.
The NIH, Retts disease (https://rarediseases.info.nih.gov/diseases/4694/atypical-rett-syndrome) accessed Dec. 9, 2018.
The NIH, Fabry disease (https://rarediseases.info.nih .gov/diseases/6400/fabry-disease) accessed Dec. 9, 2018.
The Cleveland Clinic—Mood disorders (https://my.clevelandclinic.org/health/diseases/17843-mood-disorders), accessed Dec. 9, 2018.
The Cleveland Clinic—mood disorders treatment (hUps://my.clevelandclinic.org/health/diseases/17843-mood-disorders/management-and-treatment), accessed Dec. 9, 2018.
Non-Final Office Action issued for U.S. Appl. No. 15/768,340, filed Dec. 14, 2018.
Haskell-Leuvano et al. ("Structure activity studies of the melanocortin antagonist SHU9119 modified at the 6, 7, 8 and 9 positions" Peptides 21 (2000) 49-57).
Chatterjee et al. ("Synthesis of N-methylated cyclic peptide" Nature Protocols: 432 vol. 7(3) 2012).
Thermo Scientific Protein Glycosylation (available May 5, 2012).
Grieco et al. "Design and Synthesis of Highly Potent and Selective Melanotropin Analogues of SH U-9119 Modified at position 6" U Biochem. & Biophys. Res. Commun., 20002, vol. 292, pp. 1075-1080.

\* cited by examiner

MODULATORS OF MELANOCORTIN RECEPTORS

CROSS REFERENCE

This application is a continuation and claims benefit of U.S. patent application Ser. No. 14/943,606, filed Nov. 17, 2015, the specification(s) of which is/are incorporated herein in their entirety by reference.

U.S. patent application Ser. No. 14/943,606 is a non-provisional and claims benefit of U.S. Provisional Patent Application No. 62/242,874, filed Oct. 16, 2015, the specification(s) of which is/are incorporated herein in their entirety by reference.

U.S. patent application Ser. No. 14/943,606 is also a continuation-in-part and claims benefit of U.S. Patent Application No. PCT/US15/35180, filed Jun. 10, 2015, which claims benefit of U.S. Provisional Patent Application No. 62/017,137, filed Jun. 25, 2014, and U.S. patent application Ser. No. 14/300,991, filed Jun. 10, 2014, the specification(s) of which is/are incorporated herein in their entirety by reference.

REFERENCE TO A SEQUENCE LISTING

Applicant asserts that the written copy of the sequence listing is identical to the sequence listing in computer readable form found on the accompanying computer text file, entitled UNIA_15_38_CON_Sequence_Listing_ST25.

FIELD OF THE INVENTION

The present invention relates to modulators of melanocortin receptors (MCR), in particular, to an N-methylated variation of a cyclic peptide and analogues thereof that are modulators for MC5R.

BACKGROUND OF THE INVENTION

The melanocortin system remains a challenging target for rational peptide and peptidomimetic design as the 3D-topographical requirements for specific melanocortin receptor subtype recognition have not been fully elucidated. Nevertheless, the numerous multifaceted physiological functions of the five known subtypes of human melanocortin receptors (hMC1-5R) continue to provide a strong stimulus for further development of potent and selective melanocortin agonists and antagonists.

On the other hand, development of selective ligands to melanocortin system bears intrinsic challenges due to conserved amino acid sequences and their structural similarity contained in the 7 transmembrane GPCR fold. Unlike other protein targets, hMCRs, known to be the smallest GPCRs have separate natural agonist and antagonist molecules for functional regulation. This aspect of hMCRs imposes a second dimension on melanocortin ligands for achieving selectivity not only to receptor subtype but also between the required agonistic and antagonistic properties. Designing such molecules which possess both functional selectivity and hMCR subtype selectivity from a four residue hMCR recognition sequence His-Phe-Arg-Trp is very demanding and necessitates to experiment with every possible molecule designing tool in peptide chemistry.

Great efforts have been made in the last decade to develop selective melanotropin peptides by following various general approaches. Application of such strategies has resulted in the development of cyclic peptides, such as Ac-Nle$^4$-c[Asp$^5$, D-Nal (2')$^7$, Lys$^{10}$]α-MSH(4-10)-NH$_2$ (SHU9119). Although lacking exclusive receptor subtype selectivity, SHU9119 has been extensively used in understanding the combined functional aspects of hMCRs. A proper insight into the structure driven responses of melanocortin subtypes requires a systematic perturbation of ligand conformation. To accomplish this, the present invention is considered to modulate the peptide conformation and the functional side chain disposition of SHU9119 peptide by N-methylation of the backbone amide NHs.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

Melanocortin receptors, MC1-5R are a family of five receptor compounds of the melanocortin receptor system. Prior to the invention, it has been difficult to target the receptors independently of one another. The key difference between the present invention and similar compounds is that the present invention is specific to individual types of melanocortin receptors, specifically to MC5R. An N-methylated form of SHU9119 and analogues thereof can antagonize MC5R. This could potentially reduce the amount of side effects incurred by the treatments involving the present invention.

According to one embodiment, the present invention features a melanocortin 5 receptor (MC5R) peptide ligand according to Formula 1:

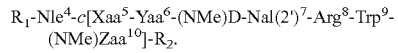

$R_1$-Nle$^4$-c[Xaa$^5$-Yaa$^6$-(NMe)D-Nal(2')$^7$-Arg$^8$-Trp$^9$-(NMe)Zaa$^{10}$]-$R_2$.

In some embodiments, $R_1$ may be an acetyl, —CO—$(CH_2)_nCH_3$, —CO—$(CH_2)_nCF_3$, or a glycosylated amino acid. Preferably, "n" can range from 1 to 6. In other embodiments, $R_2$ may be an —$CONH_2$, —COOH, or —$CH_2OH$. In one embodiment, Xaa, Yaa, and Zaa may each be a natural amino acid or an unnatural amino acid. The MC5R peptide ligand may be a cyclic peptide formed by the bridging of Xaa to Zaa via a carba, lactam, disulfide, thioether, or succinic linker. In another embodiment, the MC5R peptide ligand has a 23 to 27-membered ring.

DESCRIPTION OF PREFERRED EMBODIMENTS

Figure 1:
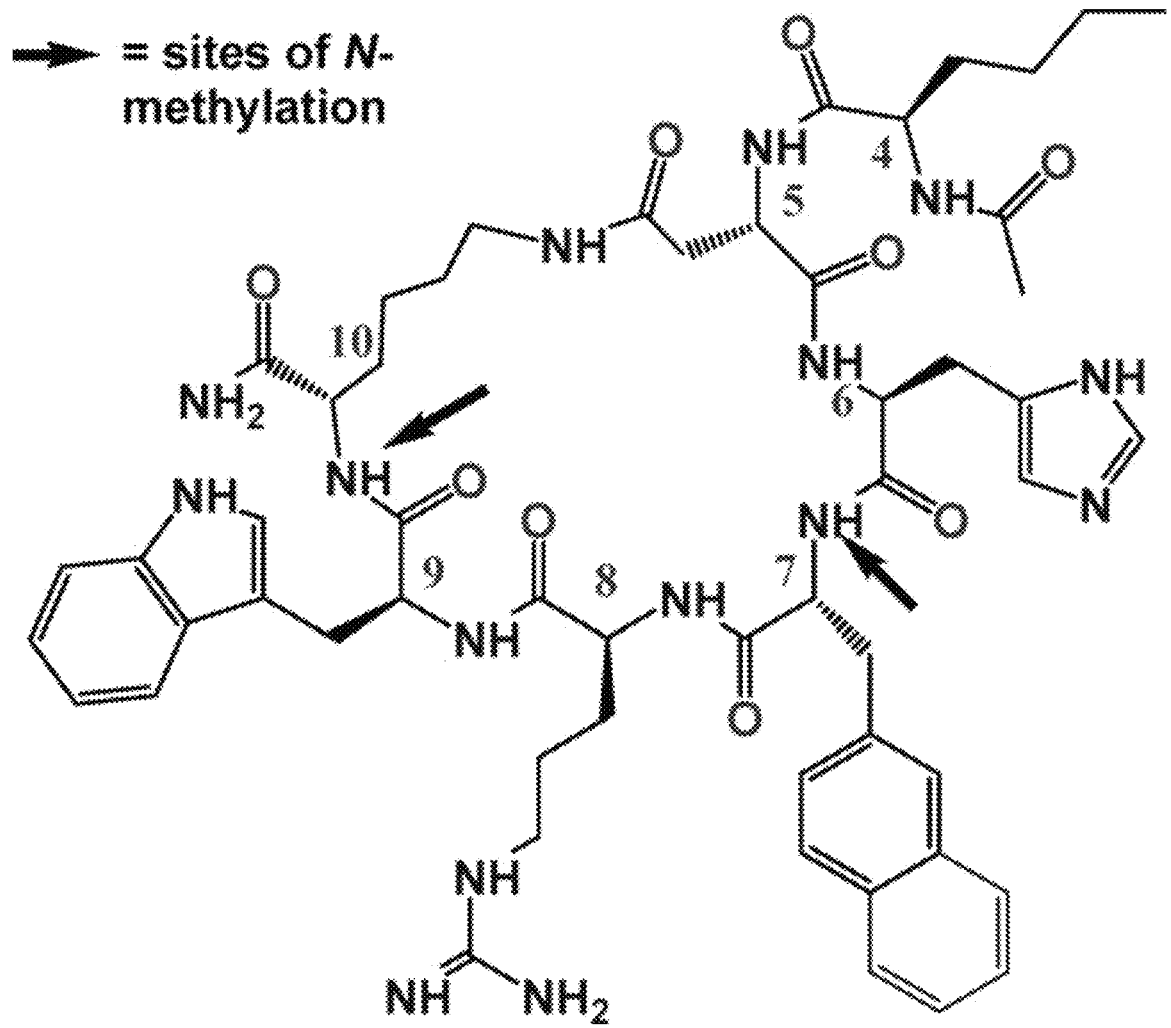
FIG. 1 shows a structure of SHU 9119. The two arrows indicate the sites of N-methylation of the backbone NHs to form one embodiment of a MC5R modulator.

Before the present compounds, compositions, articles, devices, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

Following is a list of abbreviations referred to herein:
Abu 2-aminobutyric acid
Acpc 1-aminocyclopropane carboxylic acid
Aic 2-aminoindane-2-carboxylic acid
Che 1-amino-1-cyclohexane carboxylic acid
Cpe 1-amino-1-cyclopentane carboxylic acid
Dab diaminobutyric acid
Ioc indoline-2-carboxyic acid
Oic octahydroindole-2-carboxylic acid
Orn ornithine
Tic tetrahydro-isoquinoline-3-carboxylic Acid As used herein, the term "natural amino acids" refers to the twenty amino acids that are found in nature, i.e. occur naturally. The natural amino acids are as follows: alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine. This application adheres to the IUPAC rules of standard abbreviations for amino acids.

As used herein, the term "unnatural amino acids" refers to amino acids that are not naturally encoded or found in the genetic code of any organisms. Typically, the unnatural amino acids are different from the twenty naturally occurring amino acids in their side chain functionality.

As defined herein, the term "antagonist" refers to compound that diminishes a response. The antagonist binds to the same site as the endogenous compound and diminishes or blocks the signal generated by the endogenous agent.

As defined herein, the term "N-methylation" refers to a form of alkylation wherein a methyl group, $CH_3$, replaces the hydrogen atom of the NH moiety in the backbone amide NHs of peptides.

As used herein, the term "NMe" preceding any three-letter abbreviation for an amino acid, i.e. (NMe)Lys, denotes the N-methylated form of the amino acid. As used herein, the term "Nle" refers to a Norleucine. As used herein, the term "c" or "cyclo" means cyclic, i.e. a cyclic peptide.

As used herein, the term "glycosylated" is defined as a saccharide (or sugar) covalently attached, i.e. linked, to an amino acid. Specifically, the saccharide is linked to the side-chain of the amino acid.

According to one embodiment, the present invention features a melanocortin 5 receptor (MC5R) peptide ligand according to Formula 1:

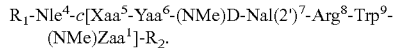

According to a preferred embodiment, the MC5R peptide ligand is an antagonist of MC5R. Alternatively, other embodiments of the MC5R peptide ligand may be agonists of MC5R.

N-Terminal Modification

In some embodiments, $R_1$ may be a glycosylated amino acid. In one aspect, the glycosylated amino acid may comprise a saccharide O-linked to a natural amino acid. For instance, the saccharide is attached to the hydroxyl group of the side-chain of the amino acid, such as Ser, Thr, or Tyr. In another aspect, the glycosylated amino acid may comprise a saccharide N-linked to a natural amino. For example, the saccharide is attached to the amine group of the side-chain of the amino acid, such as Asn or Lys. The saccharide may be a monosaccharide, a disaccharide, or an oligosaccharide. Examples of saccharides include, but are not limited to, glucose, fructose, and lactose.

In other embodiments, acetylation of the N-terminal results in $R_1$ being an acetyl. In further embodiment, $R_1$ may be $—CO—(CH_2)_nCH_3$ or $—CO—(CH_2)_nCF_3$. Preferably, "n" can range from 1 to 6.

Without wishing to limit the invention to a particular theory or mechanism, N-terminal modifications may play a role in stability, protein folding, cellular attachment, and function modulation of the MC5R peptide ligand.

C-Terminal Modification

In further embodiments, $R_2$ may be an $—CONH_2$, $—COOH$, or $—CH_2OH$. Without wishing to limit the invention to a particular theory or mechanism, C-terminal modifications, such as amidation, can enhance the biological activity of the peptide ligand, increase the ligand's stability, efficacy, and ability to enter cells, as well as increase its ability to resist enzymatic degradation.

Amino Acid Modifications

In one embodiment, Xaa may be a natural amino acid or an unnatural amino acid. For example, Xaa may be the natural amino acid Asp or Glu, or the unnatural amino acid Abu.

In another embodiment, Yaa may be a natural amino acid such as His or Pro, or an unnatural amino acid such as Oic, Ioc, Tic, Cpe, Che, Aic, and Acpc. Without wishing to limit the invention to a particular theory or mechanism, the Yaa modification can provide for a stable 13 turn-like structure and improved potency of the MC5R peptide ligand.

In a further embodiment, Zaa may be a natural amino acid such as Lys, or an unnatural amino acid such as Orn, and Dab.

In one alternate embodiment, a side-chain of the amino acid in the cyclic peptide may be halogenated. For example, if Yaa is His, then the side-chain of His may be halogenated. As another example, the side-chain of (NMe)D-Nal(2') or Trp in the cyclic peptide may be para-, meta-, or ortho-halogenated or di-halogenated. In another alternate embodiment, a side-chain of the amino acid may be glycosylated. For example, the side-chain of Lys in the cyclic peptide may be glycosylated.

It is understood that the aforementioned examples of $R_1$, $R_2$, Xaa, Yaa, and Zaa are non-limiting. For instance, Xaa, Yaa, and Zaa can be any natural amino acid or unnatural amino acid. Preferably, $R_1$, $R_2$, Xaa, Yaa, and Zaa are each selected to produce a specific MC5R peptide ligand having desired properties.

Without wishing to limit the present invention to a particular theory or mechanism, N-methylation of the backbone NHs as indicated in FIG. 1 can provide for an increase in blood-brain barrier penetration, selectivity, and stability of the MC5R peptide ligand. A non-limiting example of an MC5R peptide ligand resulting from N-methylation of sites indicated in FIG. 1 is the following peptide:

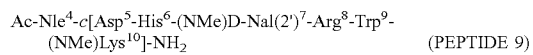 (PEPTIDE 9)

Figure 2:
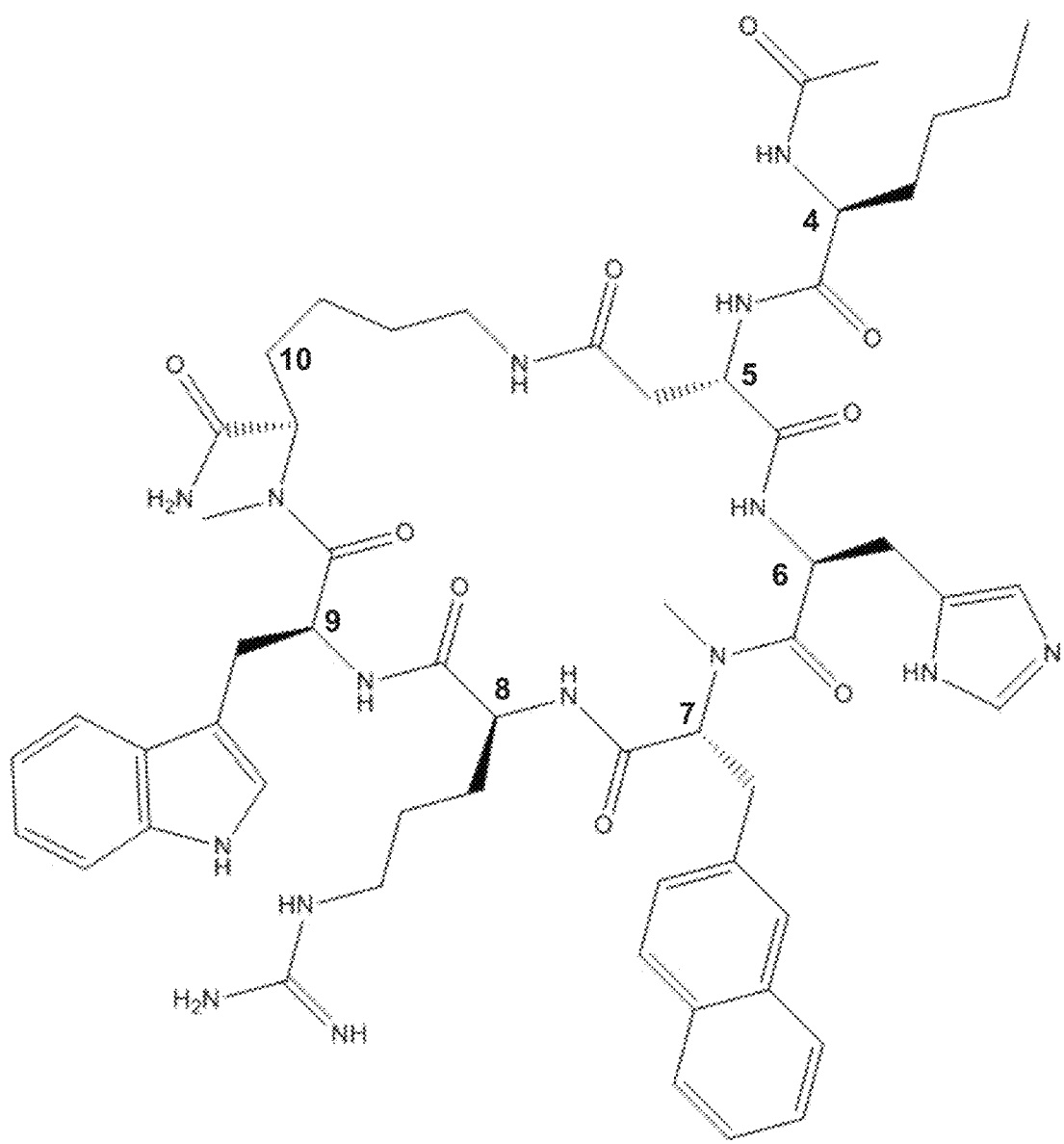
FIG. 2 shows a structure of an exemplary MC5R peptide ligand, PEPTIDE 9.

Shown in FIG. 2 is PEPTIDE 9, in which $R_1$ is an acetyl ("Ac"), $R_2$ is $—CONH_2$, Xaa is the natural amino acid "Asp", Yaa is the natural amino acid "His", and Zaa is the natural amino acid "Lys".

Cyclic Modifications

The MC5R peptide ligand is preferably a cyclic peptide formed by the bridging of Xaa to Zaa via ring closing reactions. In particular, the side chain of the Xaa residue is linked to the side chain of the Zaa residue via a linker $L_1$. In some embodiments, the linker $L_1$ is a carba, lactam, disulfide, thioether, or succinic linker. As understood by one of ordinary skill in the art, the linker is not limited to the aforementioned examples, and may depend upon the specific cyclization chemistry used to produce the cyclic peptide.

As a non-limiting example, Xaa can be linked to Zaa via an amide bond formation reaction, which may form a —(CH$_2$)—CO—NH—(CH$_2$)$_n$— bridge, where n=1, 2, 3, 4. In addition, carbon-carbon bonds, lactone, thioether, ether, disulfide and other covalent bonds can be used as a part of the ring closing reactions.

Without wishing to limit the invention to a particular theory or mechanism, the type of linker can affect the structural, chemical, and biological activity of the peptide ligand.

Ring Size Modification

Selection of Xaa and Zaa can affect the ring size of the MC5R peptide ligand. Ideally, the MC5R peptide ligand may be a 23-membered ring. For instance, as shown in FIG. 2, the MC5R peptide ligand is a 23-membered ring. In another preferred embodiment, the MC5R peptide ligand may be a 23 to 29-membered ring. As another example, if Zaa is Orn and Xaa is Glu, the MC5R peptide ligand is a 23-membered ring. As a further example, if Zaa is Lys and Xaa is Glu, the MC5R peptide ligand is a 24-membered ring.

Without wishing to limit the invention to a particular theory or mechanism, the ring size of the MC5R peptide ligand can affect the selectivity of the peptide ligand. For example, a 23-membered ring may provide a universal peptide ligand for MC1R, MC3R, MC4R, and MC5R. For a ring-size greater than 26 members, the peptide ligand may be selective for a particular melanocortin receptor, such as MC1R and MC5R.

Table 1 summarizes the modifications on the MC5R peptide ligand:

| Modification | Variable | Variable Examples |
|---|---|---|
| N-Terminal | R$_1$ | Acetyl, glycosylated amino acids, —CO—(CH$_2$)nCH$_3$, or —CO—(CH$_2$)nCF$_3$, n is 1 to 6 |
| C-Terminal | R$_2$ | —CONH$_2$, —COOH, or —CH$_2$OH |
| Amino Acid | Xaa | Asp, Glu, or Abu |
| | Yaa | His, Pro, Oic, Ioc, Tic, Cpe, Che, Aic, or Acpc |
| | Zaa | Lys, Orn, or Dab |
| | Amino acid in the cyclic peptide | Glycosylated amino acid, p-, m-, o- halogen or di-halogen substitution of a side-chain of the amino acid |
| Cyclic Linker | L$_1$ | carba, lactam, disulfide, thioether, or succinic linker |
| Ring Size | Xaa, Zaa | 23, 24, 25, 26, 27, 28, or 29-membered ring |

According to another embodiment, the present invention features a melanocortin 5 receptor (MC5R) peptide ligand according to Formula 2:

Ac-Nle$^4$-c[Asp$^5$-His$^6$-(NMe)D-Nal(2')$^7$-Arg$^8$-Trp$^9$-(NMe)Lys$^{10}$]-NH$_2$  (PEPTIDE 9)

According to another embodiment, the present invention features a melanocortin 5 receptor (MC5R) peptide ligand according to Formula 3:

R$_1$-Nle$^4$-c[Asp$^5$-His$^6$-(NMe)D-Nal(2')$^7$-Arg$^8$-Trp$^9$-(NMe)Lys$^{10}$]-R$_2$.

In one embodiment, R$_1$ may be an acetyl, a glycosylated amino acid, —CO—(CH$_2$)$_n$CH$_3$, or —CO—(CH$_2$)$_n$CF$_3$. Preferably, n can range from 1 to 6. In another embodiment, R$_2$ is an —CONH$_2$, —COOH, or —CH$_2$OH.

According to another embodiment, the present invention features a melanocortin 5 receptor (MC5R) peptide ligand according to Formula 4:

R$_1$-Nle$^4$-c[Asp$^5$-Yaa$^6$-(NMe)D-Nal(2')$^7$-Arg$^8$-Trp$^9$-(NMe)Lys$^{10}$]-R$_2$.

In one embodiment, R$_1$ may be an acetyl, a glycosylated amino acid, —CO—(CH$_2$)$_n$CH$_3$, or —CO—(CH$_2$)$_n$CF$_3$. Preferably, n can range from 1 to 6. In another embodiment, R$_2$ is an —CONH$_2$, —COOH, or —CH$_2$OH. In a further embodiment, Yaa may be a natural amino acid such as His or Pro, or an unnatural amino acid such as Oic, Ioc, Tic, Cpe, Che, Aic, and Acpc.

According to further embodiment, the present invention features a melanocortin 5 receptor (MC5R) peptide ligand according to Formula 5:

R$_1$-Nle$^4$-c[Xaa$^5$-His$^6$-(NMe)D-Nal(2')$^7$-Arg$^8$-Trp$^9$-(NMe)Zaa$^{10}$]-R$_2$.

In one embodiment, R$_1$ may be an acetyl, a glycosylated amino acid, —CO—(CH$_2$)$_n$CH$_3$, or —CO—(CH$_2$)$_n$CF$_3$. Preferably, n can range from 1 to 6. In another embodiment, R$_2$ is an —CONH$_2$, —COOH, or —CH$_2$OH. In some embodiments, Xaa may be a natural amino acid or an unnatural amino acid. For example, Xaa may be the natural amino acid Asp or Glu, or the unnatural amino acid Abu. In other embodiments, Zaa may be a natural amino acid such as Lys, or an unnatural amino acid such as Orn, and Dab.

As used herein, the term "about" refers to plus or minus 10% of the referenced number.

The disclosures of the following U.S. patent applications are incorporated in their entirety by reference herein: PCT/US15/35180 filed on Jun. 10, 2015.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A melanocortin 5 receptor (MC5R) peptide ligand according to the formula:

$$R_1\text{-Nle}^4\text{-}c[\text{Asp}^5\text{-Pro}^6\text{-(NMe)D-Nal(2')}^7\text{-Arg}^8\text{-Trp}^9\text{-(NMe)Lys}^{10}]\text{-}R_2,$$

wherein $R_1$ is an acetyl, a glycosylated amino acid, or $-CO-(CH_2)_nCH_3$, wherein n ranges from 1 to 6, wherein $R_2$ is an $-CONH_2$, $-COOH$, or $-CH_2OH$, and wherein the MC5R peptide ligand is an MC5R antagonist.

2. The MC5R peptide ligand of claim 1, wherein the glycosylated amino acid comprises a saccharide O-linked to a natural amino acid, wherein the natural amino acid is Ser, Thr, or Tyr.

3. The MC5R peptide ligand of claim 1, wherein the glycosylated amino acid comprises a saccharide N-linked to a natural amino acid, wherein the natural amino acid is Asn or Lys.

4. A melanocortin 5 receptor (MC5R) peptide ligand according to the formula:

$$\text{Ac-Nle}^4\text{-}c[\text{Asp}^5\text{-Pro}^6\text{-(NMe)D-Nal(2')}^7\text{-Arg}^8\text{-Trp}^9\text{-(NMe)Lys}^{10}]\text{-NH}_2,$$

wherein the MC5R peptide ligand is an MC5R antagonist.

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: synthetic melanocortin 5 receptor (MC5R)
      peptide ligand
<220> FEATURE:
<221> NAME/KEY: MOD_RES
<222> LOCATION: (1)..(1)
<223> OTHER INFORMATION: N-terminal modification is Acetyl, glycosylated
      amino acid, or -CO-(CH2)nCH3, wherein n ranges from 1 to 6.
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (2)..(7)
<223> OTHER INFORMATION: Cyclization
<220> FEATURE:
<221> NAME/KEY: MISC_FEATURE
<222> LOCATION: (2)..(2)
<223> OTHER INFORMATION: Xaa is Asp, Glu, or Abu.
<220> FEATURE:
<221> NAME/KEY: MISC_FEATURE
<222> LOCATION: (3)..(3)
<223> OTHER INFORMATION: Xaa is His, Pro, Oic, Ioc, Tic, Cpe, Che, Aic,
      or Acpc.
<220> FEATURE:
<221> NAME/KEY: MISC_FEATURE
<222> LOCATION: (4)..(4)
<223> OTHER INFORMATION: D-Nal(2')
<220> FEATURE:
<221> NAME/KEY: MOD_RES
<222> LOCATION: (4)..(4)
<223> OTHER INFORMATION: N-methylated
<220> FEATURE:
<221> NAME/KEY: MISC_FEATURE
<222> LOCATION: (7)..(7)
<223> OTHER INFORMATION: Xaa is Lys, Orn, or Dab.
<220> FEATURE:
<221> NAME/KEY: MOD_RES
<222> LOCATION: (7)..(7)
<223> OTHER INFORMATION: N-methylated
<220> FEATURE:
<221> NAME/KEY: MOD_RES
<222> LOCATION: (7)..(7)
<223> OTHER INFORMATION: C-terminal modification is -CONH2, -COOH, or
      -CH2OH.

<400> SEQUENCE: 1

Xaa Xaa Xaa Xaa Arg Trp Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic MC5R peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (2)..(7)
<223> OTHER INFORMATION: Cyclization
<220> FEATURE:

```
<221> NAME/KEY: MISC_FEATURE
<222> LOCATION: (4)..(4)
<223> OTHER INFORMATION: D-Nal(2')
<220> FEATURE:
<221> NAME/KEY: MOD_RES
<222> LOCATION: (4)..(4)
<223> OTHER INFORMATION: N-methylated
<220> FEATURE:
<221> NAME/KEY: MOD_RES
<222> LOCATION: (7)..(7)
<223> OTHER INFORMATION: N-methylated
<220> FEATURE:
<221> NAME/KEY: MOD_RES
<222> LOCATION: (7)..(7)
<223> OTHER INFORMATION: AMIDATION

<400> SEQUENCE: 2

Xaa Asp Pro Xaa Arg Trp Lys
1               5
```